United States Patent
Smith

(10) Patent No.: US 12,059,417 B1
(45) Date of Patent: Aug. 13, 2024

(54) BUPRENORPHINE FOR THE TREATMENT OF AUTONOMIC DYSFUNCTION

(71) Applicant: Douglas R. Smith, Charlotte, NC (US)

(72) Inventor: Douglas R. Smith, Charlotte, NC (US)

(73) Assignee: SMITH GENETICS RESEAR CH, LLC, Upperville, VA (US)

( * ) Notice: Subject to any disclaimer, the term of this patent is extended or adjusted under 35 U.S.C. 154(b) by 0 days.

(21) Appl. No.: 17/722,281

(22) Filed: Apr. 15, 2022

Related U.S. Application Data

(60) Provisional application No. 63/175,733, filed on Apr. 16, 2021.

(51) Int. Cl.
*A61K 31/485* (2006.01)
*A61P 25/00* (2006.01)

(52) U.S. Cl.
CPC .......... *A61K 31/485* (2013.01); *A61P 25/00* (2018.01)

(58) Field of Classification Search
CPC ..... A61K 31/4748; A61K 31/485; A61P 9/00; A61P 25/36
USPC ....................................................... 514/279
See application file for complete search history.

(56) References Cited

PUBLICATIONS

Lintzeris, N. et al.: Buprenorphine dosing regime for inpatient heroin withdrawal: a symptom-triggered dose titration study. Drug and Alcohol dependence, vol. 70, pp. 287-294, 2003.*
Umbricht, A. et al.: Opioid detoxification with buprenorphine, clonidine, or methadone in hospitalized heroin dpendent patients with HIV infection. Drug and Alcohol Dependence, vol. 69, pp. 263-272, 2003.*
Reece, A. S. et al.: Elevation of central arterial stiffness and vascular aging in opiate withdrawal: cross-sectional and longitudinal studies. Cardiovascular Toxicology, vol. 13, pp. 55-67, 2013.*
Keinbaum, P. et al.: Profound increase in epinephrine concentration in plasma and cardiovascular stimulation after mu-opioid receptor blockade in opioid addicted patients during Barbiturate-induced anesthesia foe acute detoxification. Anesthesiology, vol. 88, pp. 1154-1161, 1998.*
Donaldson, M.D.J. et al.: Plasma catecholamine levels in porcine Escherichiacoli septicaemia and following treatment with Buprenorphine or naloxone. Circulatory Shock, vol. 39, pp. 169-177, 1993.*
Nauts, M.D., D. "The ASAM Treatment of Opioid Use Disorder Course—Disclosure Information," FASAM (Sep. 11, 2019).
Gureje et al., Persistent pain and well-being: a World Health Organization Study in Primary Care, JAMA, 1998; 280(2): 147:51.
The American Society of Addiction Medicine's ("ASAM") definition of addiction, which was adopted in Sep. 2019, https://www.asam.org/quality-care/definition-of-addiction.
Chiara et al., Drugs abused by humans preferentially increase synaptic dopamine concentrations in the mesolimbic system of freely moving rats, Proc. Natl. Acad. Scl. USA, 1988; 85: 5274-5278.
Daglish et al., Brain dopamine response in human opioid addiction, Brit. J. Psych., 2008; 193(1): 65-73.
Watson et al., Investigating expectation and reward in human opioid addiction with [(11)C] raclopride PET, Addict. Biol., 2014; 19(6): 1032-40.
Nielsen, D. A., et al., Increased OPRM1 DNA Methylation in Lymphocytes of Methadone-Maintained Former Heroin Addicts, Neuropsychopharmacology, 2009, 34: 867-873.
Chorbov, V. M. et al., Elevated Levels of DNA Methylation at the OPRM1 Promoter in Blood and Sperm from Male Opioid Addicts, J. Opioid Manag., 2011; 7(4): 258-264.
Wachman, E.M. et al., Epigenetic Variation in the Mu-opioid Receptor Gene in Infants with Neonatal Abstinence Syndrome, J. Pediatrics, 2014, 166(3): 472-478.
Wachman, E.M. et al., Epigenetic Variation in OPRM1 Gene in Opioid-Exposed Mother-Infant Dyads, Genes, Brain an Behavior, 2018, 17(7): e12476.
Sandoval-Sierra, Jose V. et al., Effect of Short-Term Prescription Opioids on DNA Methylation of the OPRM1 Promoter, Clinical Epigenetics, 2020, 12:76. https://doi.org/10.1186/s13148-020-00868-8.
He et. al., Regulation of Opiold Receptor Trafficking and Morphine Tolerance by Receptor Oligomerization, Cell, 2002, 108(2): 271-282.
Chernecky et al., Laboratory Tests and Diagnostic Procedures, 6th ed., St. Louis, MO: Elsevier Saunders; 2013:302-305 (Book: https://www.google.com/books/edition/Laboratory_Tests_and_Diagnostic_Procedur/dWHYcOJK-cgC?hl=en&gbpv=1&pg=PP1&printsec=frontcover).
The human OPRM1 genomic DNA sequence is available at NCBI, Genbank, Accession No. AY587764 (https://www.ncbi.nlm.nih.gov/nuccore/AY587764.1). Printed from the Internet on Sep. 18, 2023.

* cited by examiner

*Primary Examiner* — Charanjit Aulakh
(74) *Attorney, Agent, or Firm* — FISHERBROYLES, LLP

(57) ABSTRACT

A method of treatment of a patient suffering from autonomic dysfunction is described. The method of treatment can include the steps of initially evaluating the patient and administering buprenorphine to treat the patient, for example, daily. The patient undergoing such treatment is subjected to monitoring. The monitoring of the patient may be on a periodic basis, for example, a weekly basis, a daily basis, or on a real-time basis. Such monitoring may be through any one or combination of a plurality of bodily measurements that includes, for example, heart rate variability or blood catecholamine concentrations. Monitoring of the patient may also occur remotely. Methods are also described for determining whether the amount of buprenorphine provided to the patient may be tapered.

21 Claims, 8 Drawing Sheets

BUPRENORPHINE FOR THE TREATMENT OF AUTONOMIC DYSFUNCTION

CROSS REFERENCE TO RELATED APPLICATIONS

This application claims the benefit of U.S. Provisional Application No. 63/175,733 filed on Apr. 16, 2021, which is incorporated by reference as if fully set forth herein.

TECHNICAL FIELD

Described herein is a method of treatment of individuals suffering from autonomic dysfunction, more specifically, a method for treatment of individuals suffering from autonomic dysfunction by administering a partial opioid agonist. In certain embodiments, buprenorphine is used in the treatment of autonomic dysfunction caused by opioid use and subsequent cessation and/or reduction of use.

BACKGROUND

The class of medications known as opioids are either prescribed medications most often used to control pain, or purchased illegally, such as heroin. These drugs can be abused, whether they are legally obtained with a prescription from the doctor, or illegally obtained on the streets.

Opioids have been in use by humans for generations. This class of medications is defined by the ability of a compound to bind to any of the known opioid receptors in the body and produce either an agonist or partial agonist effect. For years, a recognized risk of opioid use was believed to be a condition called Opioid Use Disorder ("OUD"), otherwise referred to as Opioid Addiction or Opioid Dependency. Opioid addiction (as it has been termed) was labeled a brain disease and hypothesized as early as 1988 to involve the neurotransmitter dopamine. Indeed, the dopamine theory of addiction has been around for almost 40 years. The theory is that addiction is a disorder of the dopamine neurotransmitter system. In essence, addictions increase dopamine to such an extent that once the drug or the stimulus is gone, the body is unable to replicate the same amount of dopamine naturally.

The National Institutes of Health projects that nearly 50 million adults in the United States alone have chronic or severe pain with over 25 million American adults reporting chronic daily pain in the past 3 months. While the overall national opioid dispensing rate declined between 2012 to 2019, in 2019, the dispensing rate had fallen to the lowest in the 14 years. In 2019, 46.7 prescriptions were issued per 100 persons; which totals more than 153 million opioid prescriptions being issued in 2019. Currently the U.S. market for opioids for chronic pain management is estimated to be on the order of $10 billion.

One of the organizations involved in the field is the American Society of Addiction Medicine ("ASAM"). ASAM's definition of addiction, which was adopted in September of 2019, is "addiction is a treatable, chronic medical disease involving complex interactions among brain circuits, genetics, the environment, and an Individual's life experiences." ASAM further provides that "people with addiction use substances or engage in behaviors that become compulsive and often continue despite harmful consequences."

The four foundations of the above definition are brain circuits, genetics, the environment, and life experiences. Notably, the ASAM definition is merely an adopted definition backed by little scientific evidence. The scant evidence is clear from an article published on ASAM's website. Nauts, M.D., D. "The ASAM Treatment of Opioid Use Disorder Course-Disclosure Information," FASAM (Sep. 11, 2019).

The Diagnostic and Statistical Manual of Mental Disorders, Fifth Edition ("DSM-5") is the standard classification of mental disorders used by mental health professionals in the United States. Opioid use disorder ("OUD") is a disease characterized by a problematic pattern of continued opioid misuse. According to the DSM-5, opioid use disorder involves the repeated occurrence of two or more of eleven identified problems within a twelve-month period that include (1) opioid withdrawal symptoms; (2) failing job, school or home responsibilities due to recurrent opioid use; (3) unsuccessful efforts to control opioid use; (4) opioid use in longer or in larger amounts than anticipated; (5) excessive amount of time spent getting or using the opioid, or recovering from its effects; (6) opioid tolerance; (7) opioid use in physically dangerous situations; (8) craving or strong desire to use opioids; (9) social or interpersonal problems caused by opioid effects; (10) giving up on occupational, recreational or social activities due to opioid use; and (11) continued opioid use despite knowledge of the addiction problem. Sever opiate dependence exists when six or more of these problems exist.

Anxiety and depression are common among patients having chronic pain and are risk factors for prescription opioid abuse and overdose. Indeed, people suffering from chronic pain are four times as likely to have anxiety or depression than those without chronic pain. Gureje et al., Persistent pain and well-being: a World Health Organization Study in Primary Care, JAMA, 1998; 280(2): 147:51.

Opioid addiction exists when someone becomes dependent on opiates beyond the need to control the pain and feels a compulsive need to continue using the drugs despite numerous attempts to quit, and despite knowing that opiate use will have negative consequences. Opioid dependence is not the same as addiction. Indeed, patients suffering from OUD benefit from Medication Assisted Therapy (MAT) for long-term maintenance to prevent relapse after a medically supervised cessation of use (detoxification). MAT is a multi-pronged approach that combines approved medications with counseling and support to treat patients suffering from OUD. Methadone, buprenorphine, buprenorphine-naloxone, and naltrexone are all approved for this use.

In particular, buprenorphine and buprenorphine in combination with naloxone are currently FDA-approved in a variety of formulations for sublingual administration for the treatment of OUD, opioid "withdrawal", and chronic pain. Current FDA-approved buprenorphine formulations for opioid use disorder contain buprenorphine in combination with the Inactive ingredient naloxone which is included with the aim of deterring abuse of buprenorphine via the intravenous route. Buprenorphine is a partial opioid agonist that has a lower risk of overdose compared to full opioid agonists (e.g., morphine, hydrocodone, methadone, oxycodone) due to what is referred to as a "ceiling effect" on respiratory depression due to buprenorphine's activity as a partial opioid agonist.

Notwithstanding, at the current time, the overwhelming majority of these patients are being misdiagnosed with, for example, opioid addiction, resulting in improper treatment i.e., inaccessibility of partial opioid agonists, such as buprenorphine. The error occurs because the practitioner is diagnosing a mental health condition prior to eliminating a physical health condition.

There remains in need in the art for the accurate diagnoses and treatment of those individuals suffering from autonomic dysfunction caused by opioid use and subsequent cessation/reduction.

SUMMARY

The present invention relates to treatment of autonomic dysfunction by administering a partial opioid agonist or combination formulation. The current methods and compositions provide therapeutic compositions and methods related to treating a patient who suffers from autonomic dysfunction. In certain embodiments of the invention, the patient suffers from autonomic dysfunction caused by opioid use and subsequent cessation of said use. In other embodiments, the patient suffers from autonomic dysfunction caused by opioid use and subsequent substantial reduction of said use.

An aspect of the invention provides a method of treatment for a patient suffering from autonomic dysfunction comprising initially evaluating the patient and administering or prescribing buprenorphine to treat the patient on a needed basis. In certain embodiments of the invention, the patient is treated with buprenorphine daily (daily basis), every two days (2-day basis), every week (weekly basis), every two weeks (2-week basis), every month (monthly basis) or any other time period determined to be necessary in the treatment of the patient.

In one embodiment, the autonomic dysfunction is a subtype or type of a neuroendocrine emergency. Still further to this embodiment of the invention, the neuroendocrine emergency is an elevated state of activation or hyperstimulation of the sympathetic nervous system and the parasympathetic nervous system.

In another embodiment, the method of treatment for the patient suffering from autonomic dysfunction may additionally include monitoring the patient. In certain embodiments of the invention, the patient may be monitored on a periodic basis. Further pursuant to this embodiment of the invention, the periodic basis is at least on a weekly basis.

In other embodiments, the patient is monitored on a real-time basis. Further pursuant to this embodiment of the invention, monitoring the patient is through a direct detection of laboratory values in a plurality of bodily tissues and fluids. Still further pursuant to this embodiment, monitoring the patient may instead or additionally be through an indirect detection of any one or more of a plurality of bodily measurements.

In another embodiment, the bodily measurement may be a heart rate variability. Further pursuant to this embodiment of the invention, the heart rate variability is measured through photoplethysmography.

In still other embodiments, recommendations for treatment of the patient can be based upon any one or more of a plurality of bodily measurements including blood catecholamine concentrations, such as epinephrine and/or norepinephrine.

In certain embodiments, the method of treatment results in a reduction in autonomic dysfunction.

Another aspect provides a method of treatment of a patient suffering from autonomic dysfunction including the steps of using buprenorphine to treat the patient and monitoring the patient remotely and in real-time. Further pursuant to this embodiment of the invention, the patient is treated using buprenorphine on any one of a daily basis, a two-day basis, a weekly basis, a bi-weekly basis, a monthly basis, and any other time period determined to be necessary in the treatment of the patient. Still further pursuant to this embodiment, the patient being monitored remotely is not in the direct presence of a medical professional and a system that provides an analysis of the monitoring results.

In yet another aspect, provided herein is a method of treatment of a patient suffering from autonomic dysfunction having the steps of monitoring the patient and adjusting an amount of buprenorphine administered or prescribed to treat the patient based upon the data received from the monitoring step. In an embodiment, the monitoring the patient is on a periodic basis. Further pursuant to this embodiment, the periodic basis is at least on a weekly basis.

In another embodiment, the monitoring the patient is on a real-time basis. Further pursuant to this embodiment, the monitoring of the patient is remotely.

Other aspects and embodiments will become apparent upon review of the following description taken in conjunction with the accompanying drawings. The invention, though, is pointed out with particularity by the included claims.

BRIEF DESCRIPTION OF THE DRAWINGS

Reference will now be made to the accompanying drawings; which are not necessarily drawn to scale, and wherein.

DETAILED DESCRIPTION

Figure 1:
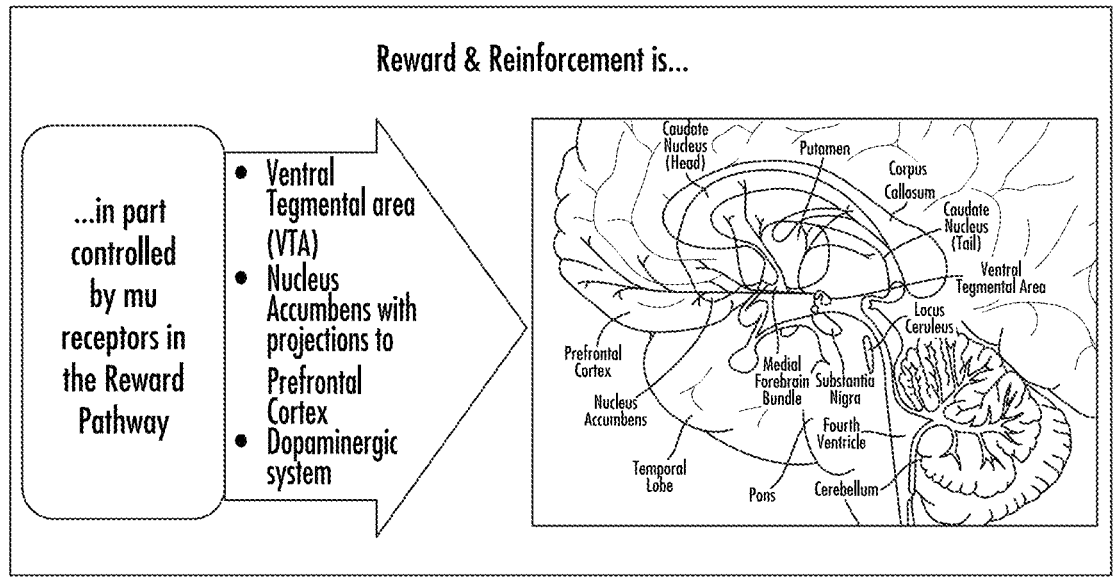
FIG. 1 is a is a diagram from the referenced course showing mu opioid receptors that are linked to mood, pain, and reward trigger pathways.

Embodiments of the present invention will be described more fully herein with reference to the accompanying drawings. Preferred embodiments of the invention may be described, but this invention may, however, be embodied in many different forms and should not be construed as limited to the embodiments set forth herein. Rather, these embodiments are provided so that this disclosure will be thorough and complete, and will fully convey the scope of the invention to those skilled in the art. The embodiments of the invention are not to be interpreted in any way as limiting the invention.

As used in the specification and in the appended claims, the singular forms "a", "an", and "the" include plural referents unless the context clearly indicates otherwise. For example, reference to "an opioid" may include a plurality of such opioids.

It will be understood that relative terms may be used herein to describe one element's relationship to another element as, for example, may be illustrated in the Figures. It will be understood that relative terms are intended to encompass different orientations of the elements in addition to the orientation of elements as illustrated in the Figures. It will be understood that such terms can be used to describe the relative positions of the element or elements of the invention and are not intended, unless the context clearly indicates otherwise, to be limiting.

Embodiments of the present invention are described herein with reference to various perspectives, including, for example, perspective views that are representations of idealized embodiments of the present invention. As a person having ordinary skill in the art would appreciate, variations from or modifications to the shapes as illustrated in the Figures or the described perspectives are to be expected in practicing the invention. Such variations and/or modifications can be the result of manufacturing techniques, design considerations, and the like, and such variations are intended to be included herein within the scope of the present invention and as further set forth in the claims that follow. The articles of the present invention and their respective components described or illustrated in the Figures are not intended to reflect a precise description or shape of the component of an article and are not intended to limit the scope of the present invention.

Although specific terms are employed herein, they are used in a generic and a descriptive sense only and not for purposes of limitation. All terms, including technical and scientific terms, as used herein, have the same meaning as commonly understood by one of ordinary skill in the art to which this invention belongs unless a term has been otherwise defined. It will be further understood that terms, such as those defined in commonly used dictionaries, should be interpreted as having a meaning as commonly understood by a person having ordinary skill in the art to which this invention belongs. It will be further understood that terms, such as those defined in commonly used dictionaries, should be interpreted as having a meaning that is consistent with their meaning in the context of the relevant art and the present disclosure. Such commonly used terms will not be interpreted in an idealized or overly formal sense unless the disclosure herein expressly so defines otherwise.

The class of medications known as the opioids have been in use by humans for generations. This class of medications is defined by the ability of a compound to bind to any of the known opioid receptors in the body and produce either an agonist or partial agonist effect. For years, a recognized risk of opioid use was believed to be a condition called Opioid Use Disorder ("OUD"), otherwise referred to as Opioid Addiction. This Oploid Addiction, as all addictions, was believed to be a brain disease, believed by some in the field to involve the neurotransmitter Dopamine. The American Society of Addiction Medicine's ("ASAM") definition of addiction, which was adopted in September of 2019, is "addiction is a treatable, chronic medical disease involving complex interactions among brain circuits, genetics, the environment, and an individual's life experiences." ASAM further provides that "people with addiction use substances or engage in behaviors that become compulsive and often continue despite harmful consequences." https://www.asam.org/quality-care/definition-of-addiction The ASAM definition of addiction is generally applied to the specific definition of opioid addiction. The four foundations of the definition of addiction are brain circuits, genetics, the environment, and life experiences. However, it is noted that the definition of addiction as put forth by ASAM is an adopted definition. This definition has little scientific evidence to back it. This is particularly true when it comes to the science behind opioids and opioid use. As further detailed herein, there is little to no scientific evidence supporting the diagnosis of opioid addiction.

The Diagnostic and Statistical Manual of Mental Disorders, Fifth Edition ("DSM-5") is the standard classification of mental disorders used by mental health professionals in the United States. DSM-5 provides that the problematic pattern of opioid use leading to clinically significant impairment or distress, is manifested by at least two of the following, occurring within a 12-month period: opioids are often taken in larger amounts or over a longer period than was intended and a persistent desire exists or an unsuccessful effort to cut down or control opioid use (in many cases demonstrated by a great deal of time that is spent in activities necessary to obtain the opioid, use the opioid, or recover from its effects); craving, or a strong desire or urge to use opioids; recurrent opioid use resulting in a failure to fulfill major role obligations at work, school, or home; continued opioid use despite having persistent or recurrent social or interpersonal problems caused or exacerbated by the effects of opioids; Important social, occupational, or recreational activities are given up or reduced because of opioid use; recurrent opioid use in situations in which it is physically hazardous; and continued opioid use despite knowledge of having a persistent or recurrent physical or psychological problem that is likely to have been caused or exacerbated by the substance.

"Autonomic Dysfunction", "Autonomic Conflict", and "Autonomic Distress" are used herein interchangeably. The condition occurs when the autonomic nervous system (ANS), which controls functions responsible for well-being and maintaining balance, does not regulate properly. Some of the basic functions controlled by the ANS include heart rate, body temperature, breathing rate, digestion, and sensation. ANS includes both the sympathetic (SANS) and parasympathetic (PANS) autonomic nervous system. The primary responsibility of the SANS is to trigger emergency responses e.g., fight-or-flight responses to stress. The PANS conserves energy and restores tissues' for ordinary functions. "Autonomic Dysfunction", "Autonomic Conflict", and "Autonomic Distress" may be characterized by stimulation of SANS and/or PANS producing a variety of physiological conditions or symptoms. For example, it has been shown that Autonomic Conflict and/or Autonomic Dysfunction result in increased catecholamine concentrations in the blood. Terms that may be used herein to describe this physiological phenomenon (and associated physiological conditions) include but are not limited to catecholamine storm, catecholamine surge, catecholamine toxicity, norepinephrine toxicity, epinephrine toxicity, dopamine toxicity, sympathetic nervous system toxicity, sympathetic nervous system dysfunction, parasympathetic nervous system toxicity, parasympathetic nervous system dysfunction, and neuroendocrine emergency.

"Tolerance" is defined by either of the following: a need for markedly increased amounts of opioids to achieve intoxication or a markedly diminished effect with continued use of the same amount of an opioid. (The latter criterion is not considered to be met for those taking opioids solely under appropriate medical supervision.)

It is understood by all that the terms opioid addiction, opioid dependency, and opioid use disorder are three phrases for the same supposed clinical entity. Whichever of the three phrases is preferred, it is noted that scientific evidence of support is thin. ASAM offers up an old Italian study performed on mice and utilizing a methodology known as micro-dialysis. This can be seen in a document on the ASAM website entitled "The ASAM Treatment of Opioid Use Disorder Course—Disclosure Information" by Daniel Nauts, MD, FASAM (Sep. 11, 2019).

A "promoter" refers to a regulatory sequence that is involved in binding RNA polymerase to initiate transcription of a gene. A promoter may be an inducible promoter or a constitutive promoter. An "Inducible promoter" is a promoter that is active under environmental or developmental regulatory conditions.

FIG. 1 is a diagram from the referenced course showing (mu) opioid receptors that are linked to mood, pain, and reward trigger pathways. FIG. 1 depicts receptors in the brain reward pathway that are involved in dopamine regulation and implicated in the dopamine theory of addiction. This theory, which has since been contested, evolved around 1988 based upon the Italian study conducted by Chiara. Chiara et al., Drugs abused by humans preferentially increase synaptic dopamine concentrations in the mesolimbic system of freely moving rats, Proc. Natl. Acad. Sci. USA, 1988; 85: 5274-5278.

Figure 2:
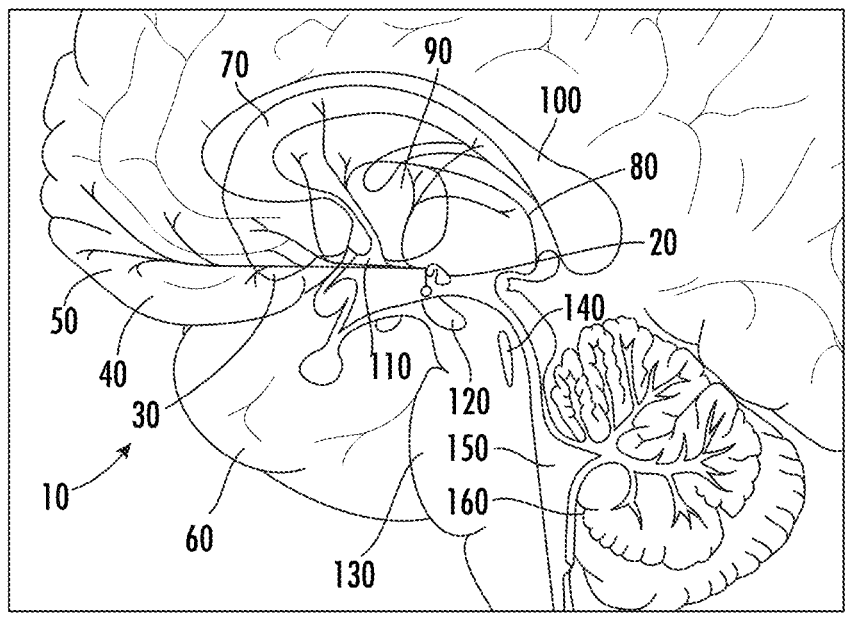
FIG. 2 is a depiction of the brain highlighted in FIG. 1.
Figure 3:
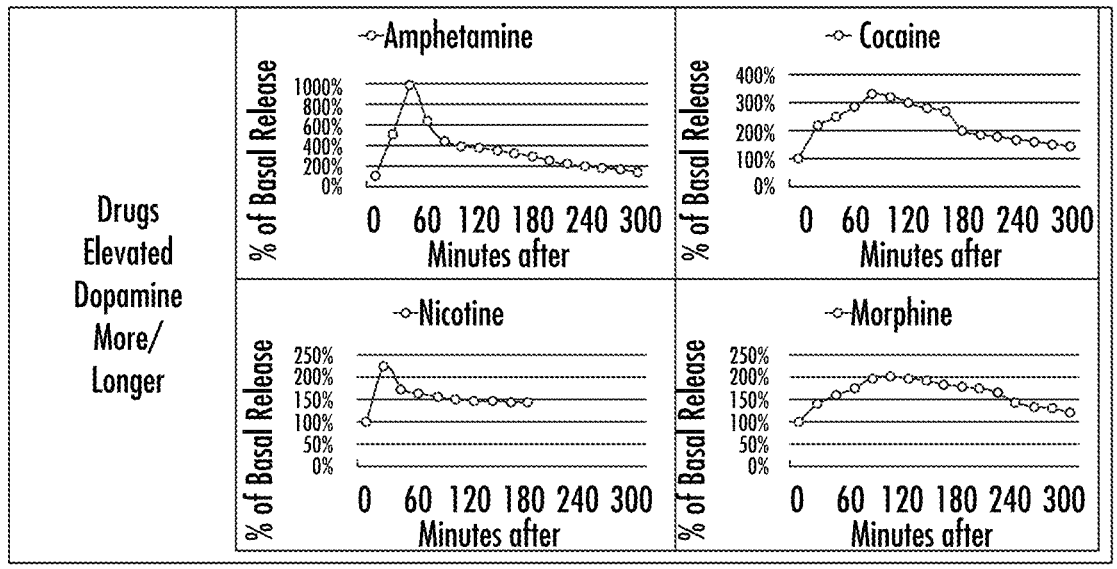
FIG. 3 are graphical representations that demonstrate the generation of elevated levels of dopamine following the use of amphetamine, cocaine, nicotine, and morphine.
Figure 4:
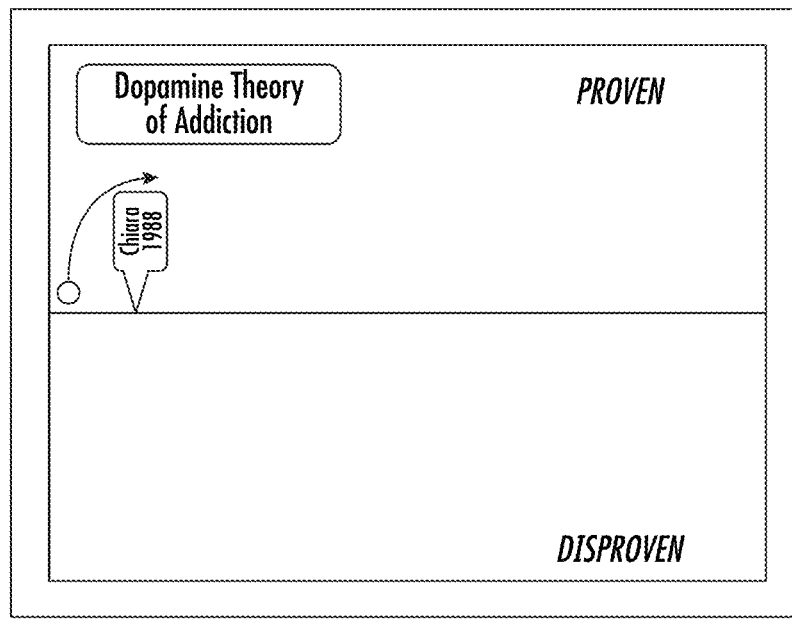
FIG. 4 is a graphical representation of the theory of addiction if only Chiara is used to support the dopamine theory of opioid addiction.

FIG. 2 is a depiction of the human brain 10 highlighted in FIG. 1. The human brain 10 includes the ventral tegmental area 20 is representative of a group of neurons located close to the floor of the midbrain. These neurons in the ventral tegmental area 20 are the basis of the dopaminergic cell bodies of the mesocorticolimbic dopamine system and other dopamine pathways theorized to be implicated in the reward circuitry of the human brain 10. The nucleus accumbens 30 is a region in the basal forebrain rostral to the preoptic area of the hypothalamus. Evidence appears to have implicated the long-term synaptic neuroadaptations in glutamatergic excitatory activity of the neurons in the nucleus accumbens 30 shell and/or core medium spiny neurons in response to chronic drug and alcohol exposure. The prefrontal cortex 40 is the cerebral cortex that covers the front part of the frontal lobe 50. The primary activity of the prefrontal cortex 40 is considered to be orchestration of thoughts and actions in accordance with internal goals, which has been implicated in planning complex cognitive behavior, personality expression, decision making, and moderating social behavior. Dopamine receptors in prefrontal cortex 40 controls the critical aspects of this decision-making area of the human brain 10. According to the dopamine theory of addiction, these sections are representative of the dopamine pathways or dopaminergic projections of the human brain 10. The graphical representations provided in FIG. 3 are based on the Chiara study suggesting that elevated levels of dopamine following the use of amphetamine, cocaine, nicotine, and morphine were shown. FIG. 4. presents a summary of the Chiara data.

The human brain 10 is a complex organ. As also shown in FIG. 2, other sections of the human brain 10, that have not been strongly implicated in the dopaminergic system include the temporal lobe 60, which is primarily engaged in deriving meanings from sensory inputs received by the human brain 10; the caudate nucleus (head) 70 in combination with the caudate nucleus (tail) 80 play a vital role in how the brain learns and the subsequent storing and processing of past memories; the putamen 90 in conjunction with the caudate nucleus 70, 80 forms the dorsal striatum and is involved in both learning and movement; the corpus callosum 100 is a bundle of nerve fibers that allow the left and right cerebral hemispheres of the human brain 10 to communicate while the medial forebrain bundle 110 is a fibrous neural pathway that passes along the midline of the forebrain to the hypothalamus, the region that extends rostrally from the ventral tegmental area 20; the substantia nigra 120 is a structure located in the midbrain that contains high levels of neuromelanin in dopaminergic neurons where the latter are synthesized and plays an important role in the regulation of movements; the pons 130 is a portion of the hindbrain that serves as a communications and coordination center between the two hemispheres of the brain; the locus ceruleus 140 also spelled locus coeruleus is a nucleus in the pons 130 of the brainstem that is involved with physiological responses to stress and panic; the fourth ventricle 150 is one of the four connected fluid-filled cavities within the human brain 10, collectively known as the ventricular system, wherein the fourth ventricle is located behind the brain stem and in front of the cerebellum 160; and the cerebellum 160 is located in the hindbrain vertebrates that plays an important role in motor control.

Recent important studies have called the dopamine theory of addiction into question. These later studies employ the highly sensitive Positron Emission Technology ("PET") scan. Two representative studies are discussed below. The first study is from 2008 led by a team headed by Mark Daglish. The Daglish study showed no surge in brain dopamine levels in response to the opioids. Daglish et al., Brain dopamine response in human opioid addiction, Brit. J. Psych., 2008; 193(1): 65-73. The second study is from 2014 led by a team headed by Ben Watson, again utilizing the PET methodology, also failed to show any surge in brain dopamine in response to the opioids. Watson et al., Investigating expectation and reward in human opioid addiction with [(11)C] raclopride PET, Addict. Biol., 2014; 19(6): 1032-40.

Figure 5:
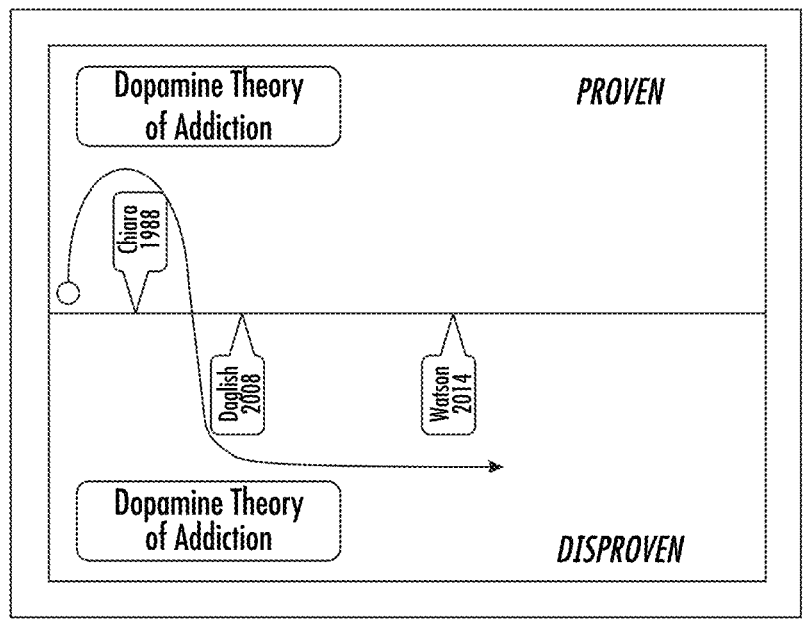
FIG. 5 is a graphical representation of the Daglesh and Watson theory of opioid addiction.

FIG. 5 provides a graphical representation as to the theory of addiction via a surge in brain dopamine that has been contested.

Recent scientific evidence questions the mental disorder focused diagnosis discussed above. Rather the studies support a conclusion that opioid products are defective causing serious and permanent damage to the DNA. We hypothesized that exposure to the opioids causes a methylation of the CpG Islands within the promoter region of the OPRM1 gene resulting in gene silencing and the formation of an abnormal (mu)opioid receptor that is no longer able to maintain balance and homeostasis within the autonomic nervous system. According to the theory, once methylation has reached a threshold, autonomic dysfunction is experienced by the individual attempting to abstain from taking the opioid. One of the characteristics of this autonomic dysfunction is epinephrine toxicity. More research must be performed to show that this theory has merit.

The human body cannot long endure autonomic dysfunction and a catecholamine surge (e.g., epinephrine toxicity) without experiencing a significant degree of suffering. The full opioid agonists offer temporary and partial relief from autonomic dysfunction, but with the common associated risks, such as addiction. Partial opioid agonists, however, such as buprenorphine, offer a longer and more definitive relief from this state of autonomic dysfunction but without the higher risk due to the ceiling effect of buprenorphine. Left untreated, autonomic dysfunction is believed to put the individual at risk of developing life-threatening opioid induced adrenal insufficiency.

Existing scientific evidence suggests an association between opioid use and methylation of the CpG Islands within the promoter region of the OPRM1 gene. The scientific evidence further supports a correlation between the methylation of the CpG Islands within the promoter region of the OPRM1 gene and the severity of symptoms experienced during the autonomic dysfunction caused by opioid use and cessation/reduction of said use. This evidence at the very least demonstrates that opioid exposure causes methylation of the CpG Islands within the promoter region of the OPRM1 gene. What has not been shown conclusively is the association between methylation and autonomic dysfunction resulting in catecholamine surge. Below is a summary of that evidence. Assuming the methylation produces gene silencing, one might expect there to be a down regulation of the OPRM1 gene. However, as will be explained below, that does not appear to be the case.

In 2009, direct sequencing of bisulfite-treated DNA showed that the percent methylation at two CpG sites was significantly associated with heroin addiction. Nielsen, D. A., et al., increased OPRM1 DNA Methylation in Lymphocytes of Methadone-Maintained Former Heroin Addicts, Neuropsychopharmacology, 2009, 34:867-873. In 2011, it was determined that increased methylation in the OPRM1 gene is associated with opioid dependence. Methylated CpG sites located in OPRM1 promoter may block the binding of Sp1 and other transcription activators. Chorbov, V. M. et al., Elevated Levels of DNA Methylation at the OPRM1 Promoter in Blood and Sperm from Male Opioid Addicts, J. Opioid Manag., 2011; 7(4): 258-264.

In 2014, it was demonstrated that increased methylation within the OPRM1 promoter is associated with worse neonatal abstinence syndrome (NAS) outcomes. Wachman, E. M. et al., Epigenetic Variation in the Mu-opioid Receptor Gene in infants with Neonatal Abstinence Syndrome, J. Pediatrics, 2014, 166(3): 472-478. In 2018, the same group replicated the previous findings, showing once again that higher levels of OPRM1 methylation, this time at specific CpG sites, are associated with increased NAS severity. Wachman, E. M. et al., Epigenetic Variation in OPRM1 Gene in Opioid-Exposed Mother-Infant Dyads, Genes, Brain an Behavior, 2018, 17(7): e12476.

There is direct evidence that the exposure to the opioids themselves causes the methylation to the CpG Islands within the promoter region of the OPRM1 gene. In 2020, Jose Vladimir Sandoval-Sierra in an article entitled "Effect of Short-Term Prescription Opioids on DNA Methylation of the OPRM1 Promoter" shows that the hypermethylation of the OPRM1 promoter is in response to opioid use and that epigenetic differences in OPRM1 and other sites are associated with a short-term use of therapeutic opioids. Sandoval-Sierra, Jose V. et al., Effect of Short-Term Prescription Opioids on DNA Methylation of the OPRM1 Promoter, Clinical Epigenetics, 2020, 12:76. And it is this study that has provided the scientific evidence for causation i.e., it is the ingestion of the opioid into the human body that is causing methylation.

Scientific evidence exists showing a link between opioid use and methylation of the CpG Islands within the promoter region of the OPRM1 gene. There is also evidence demonstrating a correlation between the level of methylation and the severity of symptoms. One would expect from the above referenced literature, that an individual suffering from the methylation in the promoter region of the OPRM1 gene would have fewer numbers of the mu-opioid receptors. Such a reduction in the number of mu-opioid receptors would be known as a down-regulation of the receptor. It was somewhat surprising then that He et al. (2016) did not find this to be the case. According to He et al., "numerous studies have demonstrated no substantial downregulation in the number of MORS (mu-opioid receptors) even in profoundly tolerant animals (for example, De Vries et al. 1993, Simantov et al. 1984; reviewed in Williams et al. 2001). Hence, it is unlikely that tolerance to morphine is mediated solely by desensitization and downregulation of the receptor." He et. al., Regulation of Opioid Receptor Trafficking and Morphine Tolerance by Receptor Oligomerization, Cell, 2016, 108(2): 271-282.

Figure 6:
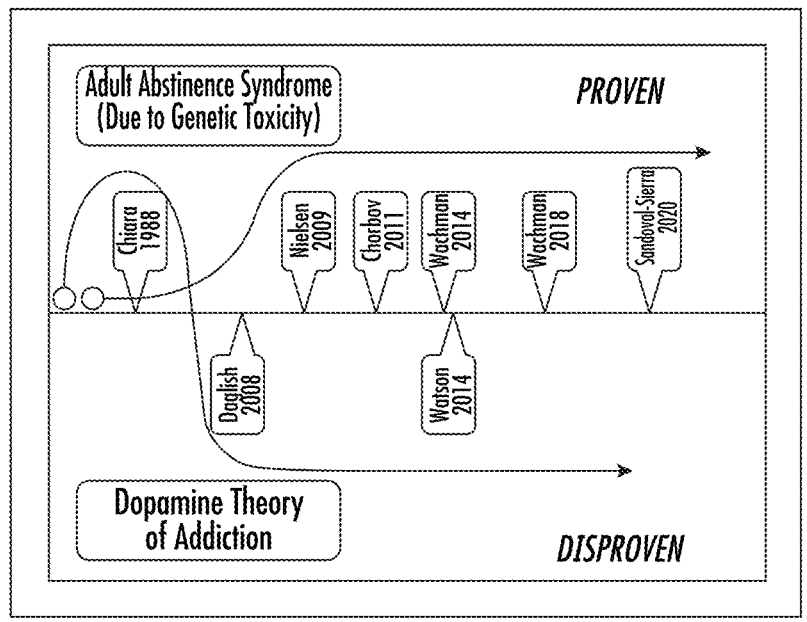
FIG. 6 is a graphical representation illustrating how autonomic dysfunction should be subject to treatment, according to certain embodiments of the invention, over the dopamine theory of addiction.

FIG. 6 is a graphical representation of the weight of evidence of genetic toxicity of opioids versus the dopamine theory of addiction. The evidence supporting defective product theory (opioid induced genetic toxicity) i.e., that opioid use causes genetic damage is overwhelming. Likewise, the evidence against opioid addiction is overwhelming, yet the mental health diagnosis of opioid addiction/dependency/use disorder is applied almost ubiquitously resulting in the administration of improper treatment regimens (i.e., behavioral treatment or therapy versus administration or prescription of opioid agonist or partial agonist, such as buprenorphine).

The recognition that the underlying disorder is not a mental health diagnosis, but a medical diagnosis is essential. Autonomic dysfunction is a physical state characterized by hyper-stimulation or activation of the autonomic nervous system—sometimes both sympathetic and parasympathetic branches. This may also be referred to as neuroendocrine emergency, a highly uncomfortable state for those afflicted producing significant alterations in behavior. It was this behavior that was misinterpreted as a state of addiction or a type of mental illness. Autonomic dysfunction is generally associated with genetic defects, for example, the autonomic dysfunction associated with dysautonomia. The inventors propose that autonomic dysfunction associated with opioid use is induced (at least in part) by methylation and any other type of genetic damage caused by the exposure to the opioids. The invention includes the use of buprenorphine for the treatment of autonomic dysfunction caused by opioid use and subsequent abstinence, cessation, or reduction. The inventive Indication for the use of buprenorphine is for the medical diagnosis autonomic dysfunction caused by opioid use and subsequent abstinence, cessation, or reduction. Another medical diagnosis may be adult abstinence syndrome with autonomic dysfunction.

As stated above, autonomic dysfunction is a state of a neuroendocrine emergency. The neuroendocrine emergency is an abnormally elevated state of activation of one or both branches of the autonomic nervous system—the sympathetic nervous system and the parasympathetic nervous system. The neuroendocrine emergency known as autonomic dysfunction is a highly uncomfortable state of being. Individuals will go to lengths to stop the symptoms. It was this behavior that was misinterpreted as a state of addiction or a type of mental illness. Buprenorphine provides a relief from this neuroendocrine emergency and the autonomic dysfunction. The endpoint for the use of the buprenorphine will be a reduction in the level of autonomic dysfunction.

Typically, the patient may be administered buprenorphine (or prescribed to betaken) on a daily basis, but any amount of time determined to be necessary may be used including, but not limited to, a bi-daily basis, a daily basis, every two days, a bi-weekly basis, a weekly basis, a bi-monthly basis, a monthly basis. Moreover, the treatment duration may be any length of time determined to be necessary by qualified medical professionals for the treatment of the patient. In addition to using buprenorphine on some predetermined basis, the patient will initially be evaluated. Furthermore, monitoring of the patient will occur on an ongoing basis. This monitoring will be specifically driven towards the end point of a reduction in the level of autonomic dysfunction. In certain embodiments of the invention, the monitoring of the patient can occur periodically on at least a daily basis, at least a weekly basis, at least a biweekly basis, at least a monthly basis, and any other periodic basis that is appropriate for the treatment of the patient. In other embodiments of the invention, the monitoring may be on a real-time basis. In still other embodiments of the invention, monitoring the patient may be remotely. As used herein, remotely is intended to mean not in the direct presence of the medical personal and/or the system that provides analysis of the results.

Abnormal levels of autonomic activity can be detected, measured, and monitored in a variety of ways. This can include direct detection and monitoring of the activity of one or both branches (SANS and/or PANS) of the autonomic nervous system. In certain embodiments of the invention, the monitoring can include direct detection and monitoring of laboratory values in a plurality of bodily tissues and fluids, for example, blood concentrations of catecholamines including for instance epinephrine and norepinephrine. In other embodiments of the invention, the monitoring includes indirect monitoring of the autonomic nervous system by such methodologies as monitoring the heart rate variability. In certain other embodiments of the invention, monitoring is intended to cover all techniques used to monitor autonomic nervous system for the ideal outcome of each patient. Left untreated, autonomic dysfunction could possibly be a risk factor for the development of opioid induced adrenal insufficiency.

In some embodiments, remote monitoring equipment (in home equipment) can be used to monitor a patient's autonomic nervous system. For example, according to certain embodiments, there are a variety of ways to monitor and measure heart rate variability. The Invention intends to encompass a multiplicity of methodologies for the measurement of heart rate variability when the results are utilized to assess the status of the autonomic nervous system. According to an embodiment of the invention, the use of a smart phone and a technology known as photoplethysmography (PPG) may be used to determine heart rate variability. In PPG, the workings of the smart phone camera are utilized to detect both transmission through and reflection from the body tissue. Based upon the level of blood perfusion, heart related information can be obtained. From the data collected, a heart rate variability can be calculated. Good heart rate variability is associated with good autonomic nervous system function. The lack of variability in heart rate is associated with abnormal function within the autonomic nervous system. The data may be either uploaded through an App or an Artificial intelligence ("AI") device, and logic can then be applied to the data. In an embodiment of the invention, from this process, predetermined recommendations for treatment can be made. Further pursuant to this embodiment of the invention, both ongoing treatment with buprenorphine and a possible tapering off of the amount of buprenorphine to be used can be accomplished. This is vastly superior over any other known current process for monitoring and tapering of a replacement drug therapy.

Monitoring of the autonomic nervous system can used to provide treatment guidance. Any and all technologies and methodologies for monitoring are included in the invention. In certain embodiments, direct measurement of autonomic nerve activity can be used for monitoring. In other embodiments of the invention, laboratory evaluation of tissue or bodily fluids are used for monitoring. In still other embodiments of the invention, indirect methods are used for monitoring. Further pursuant to this embodiment of the invention, heart rate variability may be used in the indirect monitoring of the patient.

According to an aspect of the invention, treatment with buprenorphine and remote real time patient monitoring will dramatically impact the ability to save those with life threatening symptoms. Through advancements in technology, through experience, and with the machine learning capabilities of Artificial Intelligence, utilizing data collected from the patient in real time and during a patient's normal daily activities, enables the patient to be monitored and advised on health issues. According to an embodiment of the invention, these technologies are important in advancing the human life expectancy.

As explained in more detail below, the treatment methods may be applicable to persons suffering genetic damage due to opioid use whether such damage is now known or later discovered. In an embodiment of the invention, the types of genetic damages may be due to the genetic sequence of the nucleotides, known Epigenetic changes, or Epigenetic changes yet to be determined.

As background, normal function of the OPRM1 gene in producing a normal (mu)opioid receptor, abnormal function of the OPRM1 gene methylated due to exposure to opioids, and abnormal (mu)opioid receptor treated with buprenorphine are discussed below.

Normal Function of the OPRM1 Gene in Producing a Normal (Mu)Opioid Receptor

Figure 7:
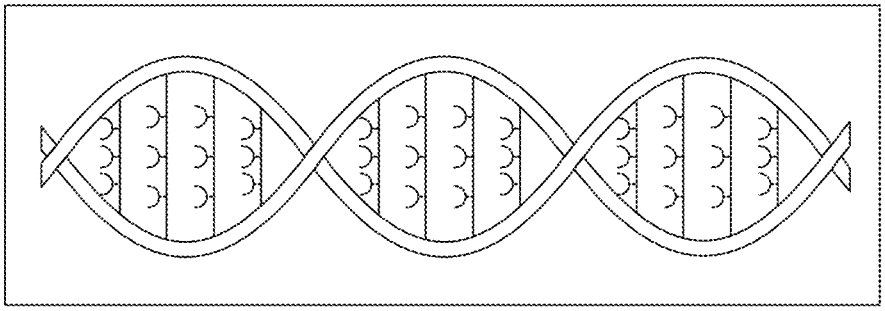
FIG. 7 is an illustration showing normal (mu)opioid receptors maintain balance and homeostasis in the autonomic nervous system.
Figure 8:
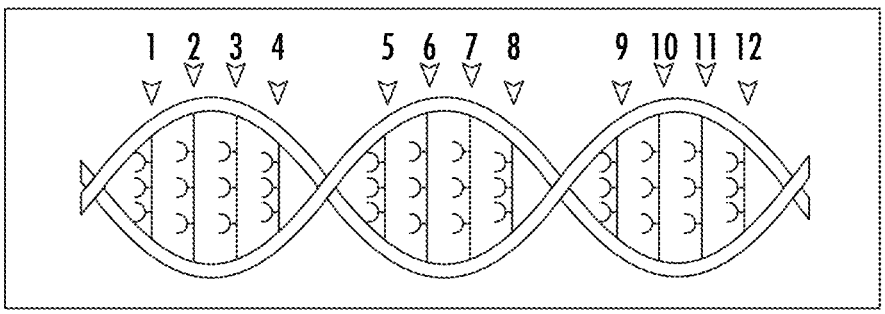
FIG. 8 is an illustration showing normal (mu) opioid receptors with all Sp1 binding cites available for binding.
Figure 9:
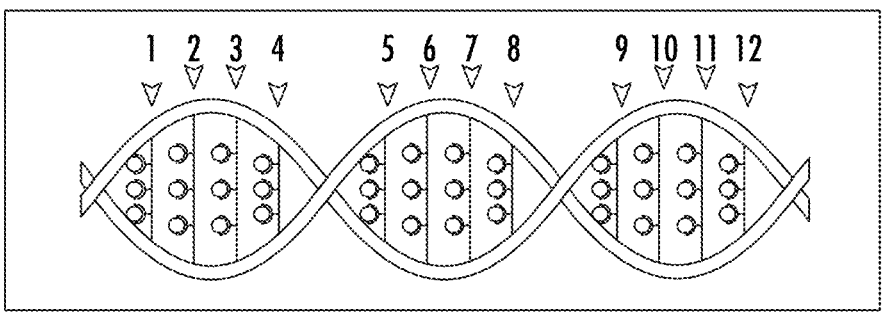
FIG. 9 is an illustration showing binding of Sp1 (Special Protein 1) to the available binding site of the normal (mu)opioid receptor.
Figure 10:
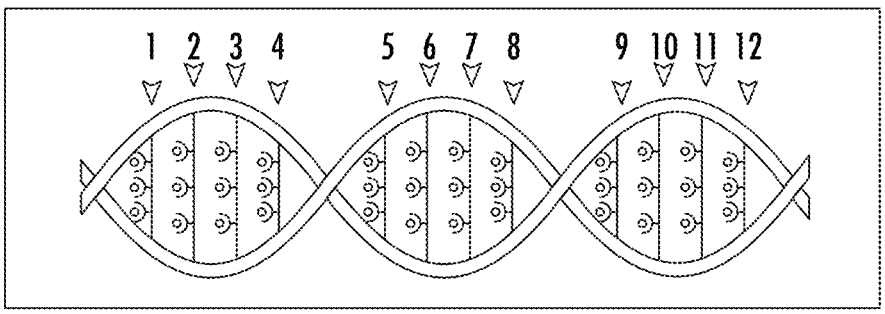
FIG. 10 is an illustration showing transcriptional machinery becomes attracted to the Sp1 bound to the Sp1 binding site of the normal (mu)opioid receptor.
Figure 11:
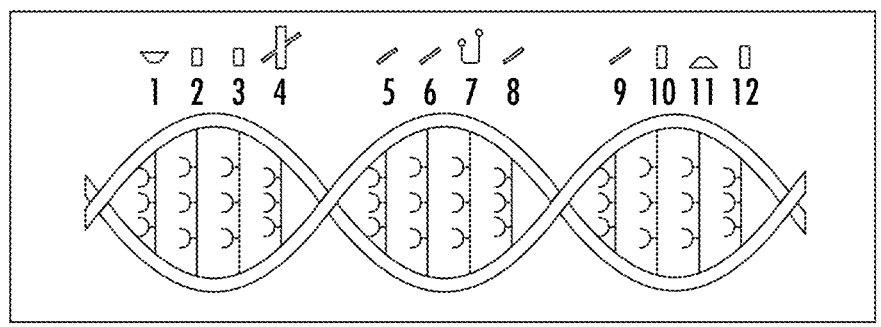
FIG. 11 is an illustration showing all twelve pieces of a protein assimilating to the normal (mu)opioid receptor (OPRM1).
Figure 12:
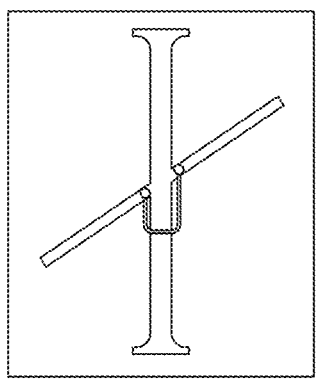
FIG. 12 is an illustration demonstrating a normal (mu) opioid receptor maintaining balance and homeostasis in the autonomic nervous system.

As illustrated in FIG. 7, the normal (mu)opioid receptor is able to maintain balance and homeostasis within the autonomic nervous system. FIG. 8 is an illustration showing normal (mu)opioid receptors with all Sp1 binding sits available for binding, while FIG. 9 is an illustration showing special protein one binds to the available binding site of the normal (mu)opioid receptor. FIG. 10 is an illustration showing transcriptional machinery becomes attracted to the Sp1 bound to the Sp1 binding site of the normal (mu)opioid receptor. FIG. 11 is an illustration showing all twelve pieces of a protein assimilating to the normal (mu)opioid receptor following transcription. FIG. 12 is an illustration demonstrating a normal (mu)opioid receptor maintaining balance and homeostasis in the autonomic nervous system.

Abnormal Function of the OPRM1 Gene Methylated from Opioid Exposure

Figure 13:
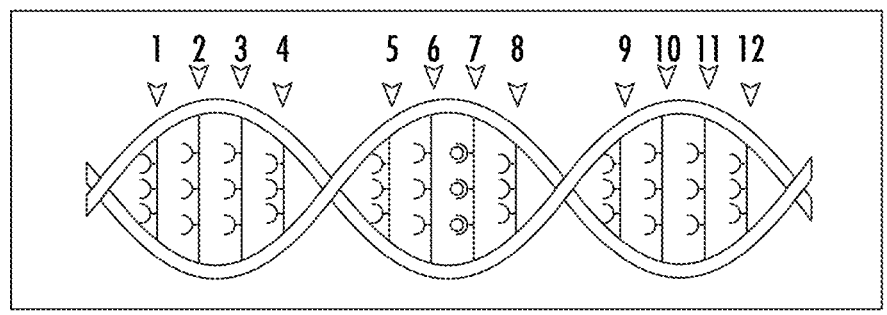
FIG. 13 is an illustration showing one of the CpG islands of the OPRM1 gene becoming methylated.

FIG. 13 is an illustration showing one of the CpG islands of the OPRM1 gene becoming methylated. This methylation may produce "partial gene silencing" whereby a receptor is produced, but it is an abnormal receptor with impaired function. As further discussed herein, the abnormal (mu) opioid receptor is no longer able to maintain balance and homeostasis within the autonomic nervous system.

Figure 14:
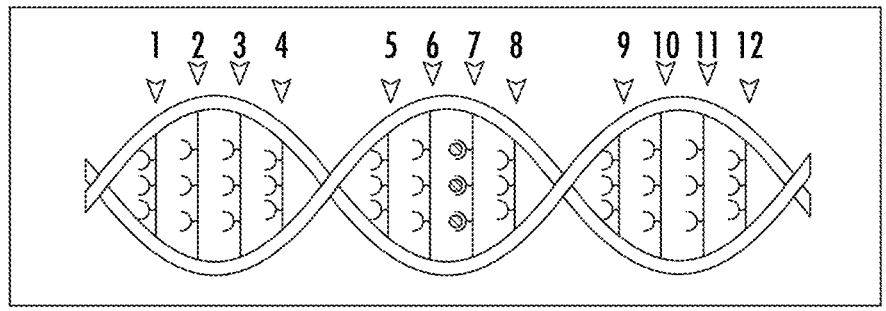
FIG. 14 is an illustration showing abnormal (mu)opioid receptors with all Sp1 binding sits available for binding except the one blocked by the methyl group.
Figure 15:
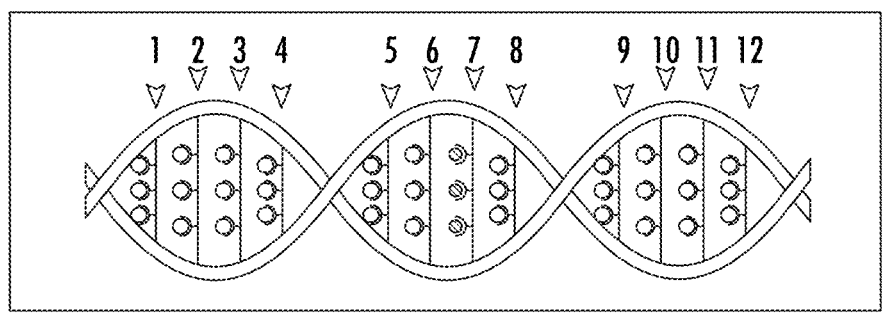
FIG. 15 is an illustration showing special protein one binds to all Sp1 site available for binding except the one blocked by the methyl group of the abnormal (mu)opioid receptor.
Figure 16:
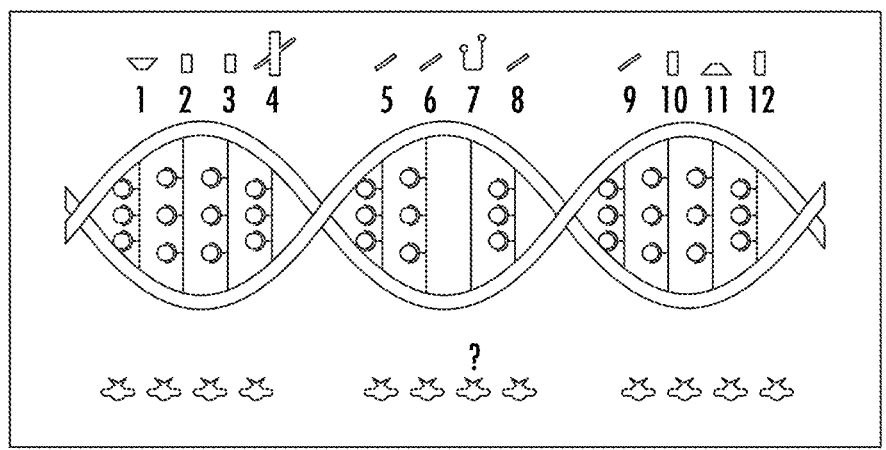
FIG. 16 is an illustration showing transcriptional machinery becomes attracted to the Sp1 bound to the Sp1 binding sites except the one blocked by the methyl group of the abnormal (mu)opioid receptor.
Figure 17:
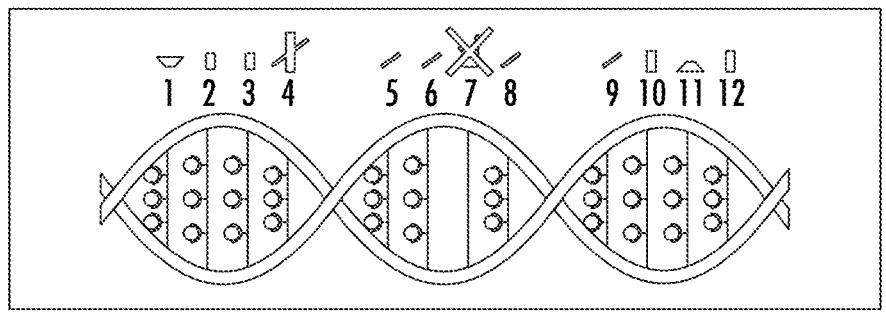
FIG. 17 is an illustration showing only eleven of the twelve pieces of a protein assimilating to the abnormal (mu)opioid receptor.
Figure 18:
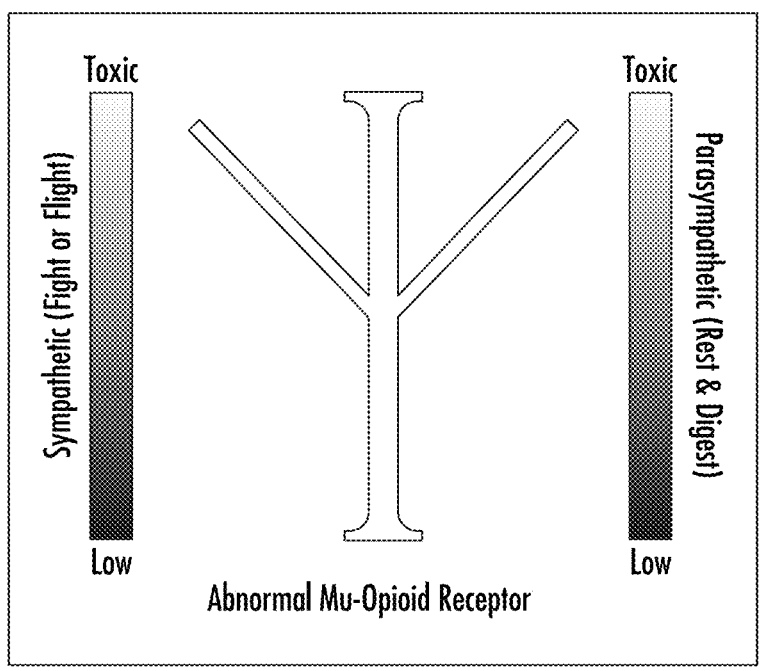
FIG. 18 is an illustration demonstrating the abnormal (mu)opioid receptor is unable to maintain balance and homeostasis within the autonomic nervous system.

FIG. 14 is an illustration showing abnormal (mu)opioid receptors with all Sp1 binding sits available for binding except the one blocked by the methyl group. FIG. 15 is an illustration showing special protein one binds to all Sp1 site available for binding except the one blocked by the methyl group of the abnormal (mu)opioid receptor. FIG. 16 is an illustration showing transcriptional machinery becomes attracted to the Sp1 bound to the Sp1 binding sites except the one blocked by the methyl group of the abnormal (mu) opioid receptor. Inasmuch, FIG. 17 is an illustration showing only eleven of the twelve pieces of a protein assimilating to the abnormal (mu)opioid receptor. Finally, FIG. 18 illustrates how the abnormal (mu)opioid receptor is unable to maintain balance and homeostasis within the Autonomic Nervous System when Oploid Abstinence is attempted. This dysfunction within the Autonomic Nervous System results in a true Neuroendocrine Emergency known as Autonomic Dysfunction. This Autonomic Dysfunction is reflected in the abnormal activity in both branches of the Autonomic Nervous System, the Sympathetic Nervous System and the Parasympathetic Nervous System. Autonomic dysfunction, and the epinephrine toxicity that results, is a condition of extreme duress and cannot long be endured by the human body.

With partial gene silencing, a population of the mu-opioid receptor may remain at or near normal, but these mu-opioid receptors have been rendered as abnormal by the methylation. In other words, the receptor was encoded and generated, but a part of the protein is defective or missing substantially impairing normal function. Partial gene silencing may result in a target molecule to be altered structurally, functionally, and structurally.

Treatment with full agonist and partial opioid agonists are possible. The full opioid agonists offer partial and temporary relief from symptoms but with risks. The partial agonist, buprenorphine, maintains a more complete and longer lasting relief with a higher level of safety due to the ceiling effect previously described.

Abnormal (Mu)opioid Receptor Treated with Buprenorphine

Figure 19:
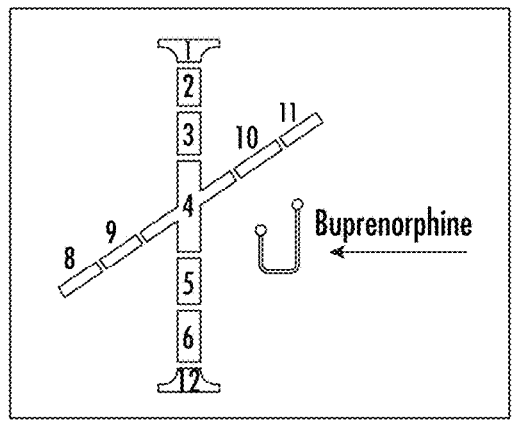
FIG. 19 is an illustration showing the addition of buprenorphine to the abnormal (mu)opioid receptor.
Figure 20:
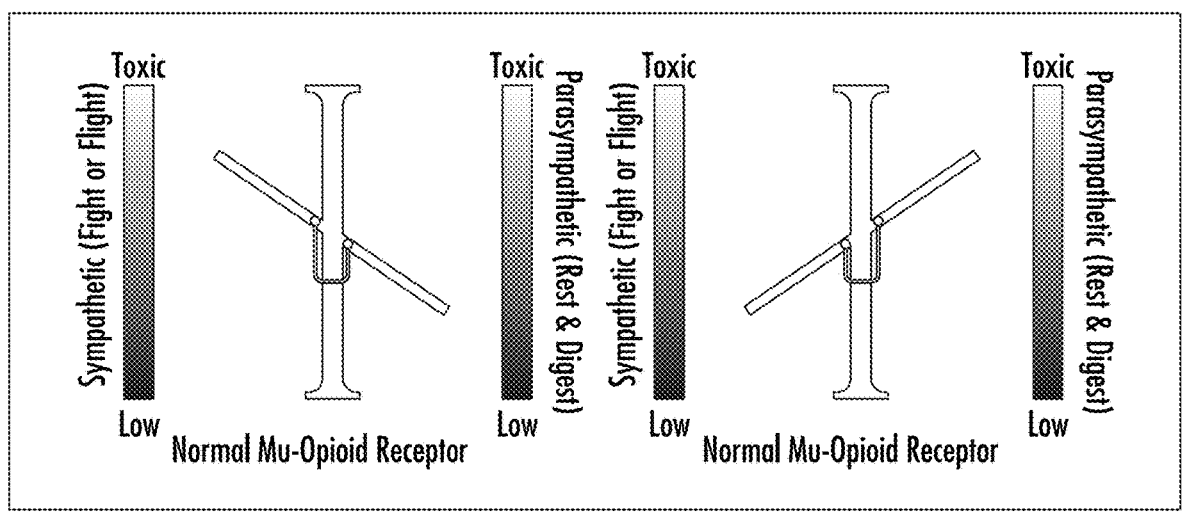
FIG. 20 is an illustration showing the abnormal (mu) opioid receptor combined with buprenorphine results in a receptor now able to maintain balance and homeostasis within the autonomic nervous system.

FIG. 19 is an illustration showing the addition of buprenorphine to the abnormal (mu)opioid receptor produced by partial gene silencing. It is thought that buprenorphine treatment results in the formation of a receptor again able to maintain balance and homeostasis within the autonomic nervous system. FIG. 20 is an illustration showing the abnormal (mu)opioid receptor combined with buprenorphine results in a receptor now able to maintain balance and homeostasis within the autonomic nervous system.

Example 1: Measuring Catecholamine Levels to Differentiate Between Autonomic Dysfunction and Opioid Addiction Many of the signs and symptoms listed above and as sympathetic in origin would be highly consistent with an episode of catecholamine toxicity. Thus, the presence or absence of catecholamine toxicity should be a determining factor in determining whether a patient suffers from opioid addiction or autonomic dysfunction during cessation or reduction of use. If the patient is truly suffering from something called opioid addiction, then the catecholamine levels during cessation/reduction will be normal. But if opioid addiction is the incorrect diagnosis and, if instead the patient is suffering from autonomic dysfunction, then the catecholamine levels during cessation/reduction will be elevated.

An episode of so-called "opioid withdrawal" may be resolved by the application of a dosage of either a full opioid agonist (i.e., hydrocodone, oxycodone, heroin, or fentanyl) or a partial opioid agonist (i.e., buprenorphine). According to the current Brain Model of Addiction, this is due to opioid craving that is the result of something called "anhedonia". The inventors hypothesized that what is occurring is not a brain function, but rather that the full or partial opioid agonist is resolving Autonomic Dysfunction. The inventors measured blood concentrations of catecholamine levels after the application of a full or partial opioid agonist to test this hypothesis. If abnormally elevated catecholamine levels are resolved after administration of a full or partial opioid agonist, then Oploid Addiction with opioid cravings due to "anhedonia" is the incorrect diagnosis. The accurate diagnosis would be Autonomic Dysfunction with opioid craving.

Case Study

The patient was a Caucasian male aged 37. The patient had been on prescribed opioids including hydrocodone and oxycodone for an orthopedic disorder. Patient had attempted to stop the opioids but became violently ill and was unable to fully stop. Patient consented to a blood draw both before and two hours after the application of a dosage of buprenorphine.

On arrival in the office, patient was ill-appearing and with initial blood pressure of 138/86, pulse of 88 and was found on examination to have mydriasis, diaphoresis, piloerection, tremor, restlessness, epiphora, excessive yawning, and rhinorrhea. A blood sample was obtained to measure catecholamine levels. Further, patient completed both an Autonomic Dysfunction Scale and the Opioid Craving Scale. Patient was administered 16 milligrams buprenorphine. A second blood sample was obtained after two hours, and both the Autonomic Dysfunction Scale and the Opioid Craving Scale were repeated. With the application of the buprenorphine, all abnormal signs and symptoms resolved including the mydriasis, diaphoresis, piloerection, tremor, restlessness, epiphora, excessive yawning, and rhinorrhea. The catecholamine concentrations and both the Autonomic Dysfunction Scale and the Opioid Craving Scale are as follows:

TABLE 2

Catecholamine Levels Prior to Buprenorphine Administration

| Test | Current Result and Flag | Units | Reference Interval |
|---|---|---|---|
| Catecholamine Frac, P$^{01}$ | | | |
| Norepinephrine, PI$^{01}$ | 1959/HIGH (Results confirmed on dilution) | pg/mL | 0-874 |
| Epinephrine, PI$^{01}$ | 107/HIGH | pg/mL | 0-62 |
| Dopamine, PI$^{01}$ | 44 | pg/mL | 0-48 |

As demonstrated in Table 2, the patient experienced what is known as a catecholamine storm with severely elevated norepinephrine and epinephrine levels. Dopamine concentrations are at the upper end of the normal range.

TABLE 3

Autonomic Distress Scale Results Prior to Buprenorphine Administration

| Symptoms | Scale (0-4) "0" non-existent and "4" most severe |
|---|---|
| I am yawning more than normal | 4 |
| My eyes are watering more than normal | 4 |
| My nose is running more than normal | 4 |
| I am having stomach cramping | 4 |
| I am vomiting | 0 |
| I have diarrhea | 4 |
| I am sweating more than normal | 4 |
| The hair on my body is standing on end | 4 |
| My heart is beating hard and fast | 3 |
| I feel anxious | 4 |
| I feel hot then cold | 4 |
| I have a tremor (shaking) | 2 |
| I feel like something bad is about to happen | 4 |
| I can't stand feeling this way | 4 |

Prior to buprenorphine administration, the patient experienced extreme autonomic distress reporting the highest severity (4) for 11 out of 14 symptoms. See Table 3.

TABLE 4

Opioid Craving Scale Results Prior to Buprenorphine Administration

| Craving | Scale (0-4) "0" non-existent and "4" most severe |
|---|---|
| If I had an opioid right now, I would take it | 4 |
| I would not be able to stop myself from taking an opioid right now | 2 |
| I would feel more in control of things if I could take an opioid right now | 4 |
| Taking an opioid right now would make me feel better | 4 |
| If I could take an opioid right now I would feel less restless | 4 |
| I am craving an opioid right now | 4 |
| Using an opioid right now would make me feel better | 4 |

Prior to buprenorphine administration, the patient experienced an extreme craving for opioids reporting the highest severity (4) for 6 out of 7 symptoms. See Table 4.

Following buprenorphine administration according to the regimen above, the patient's catecholamine profile reflected dramatically reduced concentrations of norepinephrine (833 pg/mL), epinephrine (41 pg/mL), and dopamine (>30 pg/mL). Likewise, the patient reported total abatement of autonomic distress and opioid cravings reporting each symptom and craving as "0".

DISCUSSION

Significantly, all three clinical entities, catecholamine storm, autonomic dysfunction, and opioid craving were rapidly resolved with a single dose of buprenorphine which, to the inventor's knowledge, was the first time that this has been evaluated. These findings call into question the accuracy of the diagnosis of opioid addiction—the more accurate diagnosis autonomic dysfunction with catecholamine storm and associated opioid craving. Millions of people have been improperly diagnosed and denied an appropriate treatment with buprenorphine, which would explain why the opioid crisis and the epidemic of opioid overdose deaths have not been attenuated despite the ample resources brought to bear.

Treatment Regimen

Once patients have been determined to be suffering from autonomic dysfunction, patients may be administered buprenorphine on a bi-daily, daily, every two days, a bi-weekly basis, a weekly basis, a bi-monthly basis, and/or a monthly basis to be determined by qualified medical professional. In addition to using buprenorphine on some predetermined basis, the patient will initially be evaluated. Moreover, monitoring of the patient will occur on an ongoing basis. This monitoring will be specifically driven towards the end point of a reduction in the level of autonomic dysfunction. In certain embodiments of the invention, the monitoring of the patient can occur periodically on at least a daily basis, at least a weekly basis, at least a biweekly basis, at least a monthly basis, and any other periodic basis that is appropriate for the treatment of the patient. In other embodiments of the invention, the monitoring may be on a real-time basis. In still other embodiments of the invention, monitoring the patient may be remotely. As used herein, remotely is intended to mean not in the direct presence of the medical personal and/or the system that provides analysis of the results.

Abnormal levels of autonomic activity can be detected, measured, and monitored in a variety of ways, for example, via direct detection and monitoring of the activity of branches of the sympathetic nervous system—both sympathetic and parasympathetic. In certain embodiments of the invention, the monitoring can include direct detection and monitoring of laboratory values (e.g., blood catecholamine concentrations) in a plurality of bodily tissues and fluids. In other embodiments of the invention, the monitoring includes indirect monitoring of the autonomic nervous system by such methodologies as monitoring the heart rate variability and through a plurality of equipment. In certain other embodiments of the invention, monitoring is intended to cover all types of sympathetic nervous system monitoring and for the ideal outcome of each patient. Upon information and belief, left untreated, autonomic dysfunction can be a risk factor for the development of opioid induced adrenal insufficiency.

While direct measurement of nerve activity and measurement of lab values have both been part of the medical landscape for some time, utilizing equipment in the home and to monitor the status of the autonomic nervous system is a novel concept in and of itself. For example, according to certain embodiments of the invention, there are a variety of ways to determine heart rate variability. The invention intends to encompass a multiplicity of methodologies for the measurement of heart rate variability when the results are utilized to assess the status of the autonomic nervous system. According to an embodiment of the invention, the use of a smart phone and a technology known as photoplethysmography (PPG) may be used to determine heart rate variability. In PPG, the workings of the smart phone camera are utilized to detect both transmission through and reflection from the body tissue. Based upon the level of blood perfusion, heart related information can be obtained. From the data collected, a heart rate variability can be calculated. Good heart rate variability is associated with good autonomic nervous system function. The lack of variability in heart rate is associated with abnormal function within the autonomic nervous system. The data may be either uploaded through an App or an Artificial Intelligence ("AI") device, and logic can then be applied to the data. In an embodiment of the invention, from this process, predetermined recommendations for treatment can be made. Further pursuant to this embodiment of the invention, both ongoing treatment with buprenorphine and a possible tapering off of the amount of buprenorphine to be used can be accomplished. This is vastly superior over any other known current process for monitoring and tapering of a replacement drug therapy. It is but one more example of how the invention advances the art and improves the quality of life for a large number of people suffering from autonomic dysfunction.

In an embodiment of the invention, monitoring of the autonomic nervous system is used to provide additional guidance regarding, for example, other components of the patient's comprehensive treatment regimen e.g., buprenorphine. In certain embodiments of the invention, direct measurement of autonomic nerve activity is used for monitoring. In other embodiments of the invention, laboratory evaluation of tissue or bodily fluids are used for monitoring. In still other embodiments of the invention, indirect methods are used for monitoring. Further pursuant to this embodiment of the invention, heart rate variability may be used in the indirect monitoring of the patient.

According to an aspect of the invention, treatment with buprenorphine and remote real time patient monitoring will dramatically impact the ability to rescue and save the individuals caught up with the opioids. Through advancements in technology, through experience, and with the machine learning capabilities of Artificial intelligence, utilizing data collected from the patient in real time and during a patient's normal daily activities, enables the patient to be monitored and advised on health issues. According to an embodiment of the invention, these technologies are important in advancing the human life expectancy. One of the first roles of this tool will be in ending the opioid crisis.

The methods of treatment of the invention may also be applied to patients suffering genetic damage due to opioid use whether such damage is now known or later discovered. In an embodiment of the invention, the types of genetic damages may be due to the genetic sequence of the nucleotides, known Epigenetic changes, or Epigenetic changes yet to be determined.

In certain embodiments of the invention, combination treatment with the medication and remote monitoring of the autonomic dysfunction. In certain other embodiments of the invention, the data along with artificial intelligence is stored in a cloud arrangement. The invention represents a major step forward in the care and treatment of millions of people suffering from autonomic dysfunction. The invention is expected dramatically and permanently to decrease the death rate from opioid overdose.

In another aspect of the invention, the autonomous nervous system is monitored for the purpose of providing guidance in tapering the amount of buprenorphine used in the treatment of the patient. Any and all methods for such monitoring as further described herein may be used in this assessment of the patient.

In other aspects, the invention can be described as follows:

Claim 1—A method of treatment for a patient suffering from autonomic dysfunction caused by opioid use and subsequent cessation of said use comprising: Initially evaluating the patient;
  determining if the patient suffers from autonomic dysfunction; and administering buprenorphine to treat the patient if said patient suffers from autonomic dysfunction.

Claim 2—The method of claim 1, wherein said determine step comprises obtaining a blood sample and measuring blood catecholamine concentrations.

Claim 3—The method of claim 2, wherein the catecholamines are selected from the group consisting of epinephrine and norepinephrine.

Claim 4—The method of claim 1, wherein said catecholamine concentrations are elevated above a normal range.

Claim 5—The method of claim 1, additionally comprising monitoring the patient.

Claim 6—The method of claim 5, wherein monitoring the patient is on a periodic basis.

Claim 7—The method of claim 6, wherein the periodic basis is at least on a weekly basis.

Claim 8—The method of claim 5, wherein monitoring the patient is on a real-time basis.

Claim 9—The method of claim 5, wherein monitoring the patient is through a direct detection of laboratory values in a plurality of bodily tissues and fluids.

Claim 10—The method of claim 5, wherein the monitoring the patient is through an indirect detection of any one or more of a plurality of bodily measurements.

Claim 11—The method of claim 10, wherein the bodily measurement is a heart rate variability.

Claim 12—The method of claim 11, wherein the heart rate variability is measured through photoplethysmography.

Claim 13—The method of claim 10, additionally comprising making recommendations for treatment based upon the any one or more of a plurality of bodily measurements.

Claim 14—The method of claim 1, wherein the method of treatment results in a reduction in autonomic dysfunction.

Claim 15—A method of treatment of a patient suffering from autonomic dysfunction caused by opioid use and cessation comprising:
  using buprenorphine to treat the patient, and
  monitoring the patient remotely and in real-time.

Claim 16—The method of claim 15, wherein the patient being monitored remotely is not in the direct presence of at least one of a medical person and a system that provides an analysis of the monitoring results.

Claim 17—A method of treatment of a patient suffering from autonomic dysfunction comprising
monitoring the patient, and
adjusting an amount of buprenorphine used to treat the patient base upon the data received from the monitoring step.

Claim 18—The method of claim 17, wherein monitoring the patient is on at least one of a periodic basis and a real-time basis.

Claim 19—The method of claim 17, wherein monitoring the patient is remotely.

Claim 20—The method of claim 19, wherein the patient being monitored remotely is not in the direct presence of at least one of a medical person and a system that provides an analysis of the monitoring results.

Many modifications and other embodiments of the invention set forth herein will come to mind to one skilled in the art to which this invention pertains having the benefit of the teachings presented in the descriptions herein. It will be appreciated by those skilled in the art that changes could be made to the embodiments described herein without departing from the broad inventive concept thereof. Therefore, it is understood that this invention is not limited to the particular embodiments disclosed, but it is intended to cover modifications within the spirit and scope of the present invention as defined by the included claims.

That which is claimed:

1. A method of treatment of a patient suffering from autonomic dysfunction caused by opioid use and subsequent cessation of said use comprising:
   a) initially evaluating the patient and obtaining a blood sample from said patient;
   b) administering one or more surveys to the patient to determine subjective autonomic distress and/or opioid craving;
   c) assaying the blood sample to determine concentrations of one or more catecholamines comprising norepinephrine;
   d) comparing said catecholamine concentrations to a reference catecholamine concentration range, wherein said reference range for norepinephrine is 0-874 pg/mL;
   e) administering buprenorphine to treat the patient if 1) said subjective autonomic distress and/or opioid craving is elevated; and 2) said norepinephrine concentration is greater than 900 pg/mL.

2. The method of claim 1, wherein said one or more catecholamines further comprises epinephrine and wherein said reference catecholamine concentration range is 0-62 pg/mL for epinephrine.

3. The method of claim 2, wherein said buprenorphine is administered to treat the patient if 1) said subjective autonomic distress and/or opioid craving is elevated; and 2) said norepinephrine concentration is greater than 900 pg/mL and said epinephrine concentration is greater than 100 pg/mL.

4. A method of using buprenorphine to treat a patient with autonomic dysfunction comprising the steps of:
   a) initially evaluating the patient and obtaining a blood sample from said patient;
   b) administering one or more surveys to the patient to determine subjective autonomic distress and/or opioid craving;
   c) assaying the blood sample to determine concentrations of one or more catecholamines comprising norepinephrine;
   d) comparing said catecholamine concentrations to a reference catecholamine concentration range, wherein said reference range for norepinephrine is 0-874 pg/mL; and
   e) administering buprenorphine to treat the patient if 1) said subjective autonomic distress and/or opioid craving is elevated; and 2) said norepinephrine concentration is greater than 900 pg/mL.

5. The method of claim 4, wherein said one or more catecholamines further comprises epinephrine and wherein said reference catecholamine concentration range is 0-62 pg/mL for epinephrine.

6. The method of claim 4 wherein said buprenorphine is administered to treat the patient if 1) said subjective autonomic distress and/or opioid craving is elevated; and 2) said norepinephrine concentration is greater than 900 pg/mL and said epinephrine concentration is greater than 100 pg/mL.

7. The method of claim 4 further comprising the step of f) monitoring the patient.

8. The method of claim 7 wherein said monitoring is performed remotely and in real time.

9. The method of claim 8 further comprising the step of g) adjusting an amount of buprenorphine used to treat the patient based upon the data received from the monitoring step.

10. The method of claim 1, wherein the patient is treated with buprenorphine daily.

11. The method of claim 1 further comprising the step of f) monitoring the patient.

12. The method of claim 1 further comprising the step of g) adjusting an amount of buprenorphine used to treat the patient based upon the data received from the monitoring step.

13. The method of claim 11, wherein monitoring the patient is on a periodic basis.

14. The method of claim 11, wherein monitoring the patient is on a real-time basis.

15. The method of claim 11, wherein monitoring the patient is through a direct detection of laboratory values in a plurality of bodily tissues and fluids.

16. The method of claim 11, wherein the monitoring the patient is through an indirect detection of any one or more of a plurality of bodily measurements.

17. The method of claim 16, wherein the bodily measurement is a heart rate variability.

18. The method of claim 17, wherein the heart rate variability is measured through photoplethysmography.

19. The method of claim 18, further comprising the step of h) making recommendations for treatment based upon the any one or more of a plurality of bodily measurements.

20. The method of claim 1, wherein the method of treatment results in a reduction in autonomic dysfunction.

21. A method of treatment of a patient suffering from autonomic dysfunction comprising:
   a) initially evaluating the patient and obtaining a blood sample from said patient;
   b) administering one or more surveys to the patient to determine subjective autonomic distress and/or opioid craving;
   c) assaying the blood sample to determine concentrations of one or more catecholamines comprising norepinephrine;
   d) comparing said catecholamine concentrations to a reference catecholamine concentration range, wherein said reference range for norepinephrine is 0-874 pg/mL; and e) administering buprenorphine to treat the patient if 1) said subjective autonomic distress and/or opioid craving is elevated; and 2) said norepinephrine concentration is greater than 900 pg/mL.

* * * * *